(12) United States Patent
Wondisford et al.

(10) Patent No.: US 6,284,491 B1
(45) Date of Patent: Sep. 4, 2001

(54) BIOLOGICALLY ACTIVE SYNTHETIC THYROTROPIN AND CLONED GENE FOR PRODUCING SAME

(75) Inventors: Fredric E Wondisford; Bruce D. Weintraub, both of Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/569,141

(22) Filed: May 11, 2000

Related U.S. Application Data

(63) Continuation of application No. 08/310,923, filed on Sep. 22, 1994, now Pat. No. 6,117,991, which is a continuation of application No. 08/110,639, filed on Aug. 23, 1993, now abandoned, which is a continuation of application No. 07/882,231, filed on May 8, 1992, now abandoned, which is a continuation of application No. 07/295,934, filed on Jan. 11, 1989, now abandoned.

(51) Int. Cl.⁷ ............................. C12N 15/09; C07H 21/04

(52) U.S. Cl. ..................... 435/69.4; 435/70.1; 435/360

(58) Field of Search ................................ 536/23.51, 23.1; 435/320.1, 365.1, 252.33, 69.1, 69.4, 70.1, 360

(56) References Cited

U.S. PATENT DOCUMENTS

| | | |
|---|---|---|
| 4,840,896 | 6/1989 | Reddy et al. . |
| 4,923,805 | 5/1990 | Reddy et al. . |
| 5,156,957 | 10/1992 | Reddy et al. . |
| 5,840,566 | 11/1998 | Kourides et al. . |

FOREIGN PATENT DOCUMENTS

| | | |
|---|---|---|
| 0 228 604 | 7/1987 | (EP) . |
| 62-19087 | 1/1987 | (JP) . |

OTHER PUBLICATIONS

Amr, S., et al., "Activities of Deglycosylated Thyrotropin at the Thyroid Membrane Receptor–Adenylate Cyclase System," *J. Endocrinol. Invest.*, vol. 8, 1985, pp. 537–541.

Blahd, W., et al., "Radioactive Iodine ($I^{131}$) In the Postoperative Treatment of Thyroid Cancer," *Cancer*, vol. 13, 1960, pp. 745–756.

Blahd, W., "Treatment of Malignant Thyroid Disease," *Seminars in Nuclear Medicine*, vol. IX, No. 2, Apr., 1979, pp. 95–99.

Burke, G., "The Thyrotrophin Stimulation Test," *Ann. Int. Med.*, vol. 69, 1968, pp. 1127–1139.

Catz, B., et al., "Treatment of Cancer of the Thyroid Postoperatively with Suppressive Thyroid medication, Radioactive Iodine, and Thyroid–Stimulating Hormone," *Cancer*, vol. 12, 1959, pp. 371–383.

Chin, W., et al., "Evidence for a Single Rat Thyrotropin—β–Subunit Gene: Thyroidectomy Increases its mRNA", *Biochem. Biophys. Res. Commun.*, vol. 128, No. 3, 1985 pp. 1152–1158.

Fiddes, J., et al., "The Gene Encoding the Common Alpha Subunit of the Four Glycoprotein Hormones" *Chemical Abstracts*, vol. 95, No. 13: Abstract No. 110370q, p. 234, Col. 1., Sep. 28, 1981.

Fiddes, J., et al., "The Gene Encoding the Common Alpha Subunit of the Four Glycoprotein Hormones" *J. Mol. Appl. Genet.*, vol. 1, No. 1: 3–18, 1981.

Guidon Jr., P., et al., "The Human Thyrotropin β–Subunit Gene Differs in 5' Structure from Murine TSH–β Genes," *DNA*, vol. 7, No. 10, 1988, pp. 691–699.

Gurr, J., et el., "Cloning of cDNA Encoding the Pre–β Subunit of Mouse Thyrotropin," *Proc. Natl. Acad. Sci.*, vol. 80, 1983, pp. 2122–2126.

Hayashizaki, Y., et al., "Molecular Cloning of the Human Thyrotropin–β Subunit Gene," *FEBS* 2825, Sep. 1985, vol. 188, No. 2 pp. 394–400.

Kaetzek, D., et al., "Expression of Biologically Active Bovine Luteinizing Hormone in Chinese Hamster Ovary Cells," *PNAS* Nov. 1985, vol. 82, pp. 7280–7283.

Laughlin, C. et al., "Cloning of Infections Adeno–associate Virus Gnomes in Bacterial Plasmids," *Gene* 23: (1983) 65–73.

Maurer, R., et al., "The Sequence of a Cloned cDNA for the β Subunit of Bovine Thyrotropin Predicts a Protein Containing Both NH2– and COOH–terminal Extensions," *Journ. Of Biol. Chemistry*, vol. 259, No. 8, Apr. 25, 1984, pp. 5024–5027.

Pierce, J.G. et al., "Glycoprotein Hormones: Structure and Function", *Ann. Rev. Biochem.*, 1981. 50:465–95.

Rose, R., et al., "Radioactive Iodine in the Diagnosis and Treatment of Thyroid Cancer," *Cancer*, vol. 16, 1963, pp. 896–913.

Tatsumi, K., et al., "The Structure of the Human Thryotropin β–Subunit Gene," *Gene*, vol. 73, No. 2, 1988, pp. 489–497.

Tubis, M., et al., "Serum $I^{131}$Fractionation in Metastatic Carcinoma of the Thyroid," *Cancer*, vol. 8, 1955, pp. 1115–1121.

Watanabe, S., et al., "Production of Human Thyroid–Stimulating Hormone in Chinese Hamster Ovary Cells," *Biochem. Biophys. Res. Commun.* , vol. 149, No. 3, 1987 pp. 1149–1155.

Williams, E.S., et al., "Thyroid Stimulation test with Serum Thyroxine Concentration as Index of Thyroid Response," *Brit. Med. Jour.*, vol. 4, 1969, pp. 336–338.

(List continued on next page.)

*Primary Examiner*—Laurie Scheiner
(74) *Attorney, Agent, or Firm*—Knobbe, Martens, Olson & Bear, LLP.

(57) ABSTRACT

Substantially pure recombinant TSH has been prepared from a clone comprising complete nucleotide sequence for the expression of the TSH. Diagnostic and therapeutic applications of the synthetic TSH are described.

4 Claims, 5 Drawing Sheets

OTHER PUBLICATIONS

Wondisford, F., et al., "Cloning of the Human Thyrotropin β–Subunit Gene and Transient Expression of Biologically Active Human Thyrotropin after Gene Transfection," *Molecular Endocrinology*, 1988, vol. 2, No. 1, pp. 32–39.

Wondisford, F. et al., "Isolation and Characterization of the Human Thyrotropin β–Subunit Gene," *Journ. Of Biol. Chemistry*, vol. 263, No. 25, Sep. 5, 1988, pp. 12538–12542.

Wondisford, F., et al., "Cloning of the Human Thyrotropin β–Subunit Gene and Transient Expression of Biologically Active Human Thyrotropin after Gene Transfection," *Chemical Abstracts*, vol. 108, No. 17, Abstract 108: 144501k, Apr. 25, 1988.

Wondisford, F., et al., "Thyroid Hormone Inhibition of Human Thyrotropin –Subunit Gene Expression is Mediated by a Cis–Acting Element Located in the First Exon," *Journ. Of Biol. Chemistry*, vol. 264, No. 25, Sep. 5, 1989, pp. 14601–14604.

Wondisford, F., et al., "Cloning of the Human Thyrotrofin β–subunit Gene and Transient Expression of Biologically Active Throtropin (TSH) After Transfection," *Clin. Res.*, vol. 35, No. 3, 1987, p. 649A.

BIOLOGICALLY ACTIVE SYNTHETIC THYROTROPIN AND CLONED GENE FOR PRODUCING SAME

RELATED APPLICATIONS

This application is a continuation of U.S. patent application Ser. No. 08/310,923 filed Sep. 22, 1994, now U.S. Pat. No. 6,117,991, which is a continuation of U.S. patent application Ser. No. 08/110,639 filed Aug. 23, 1993, abandoned, which is a continuation of U.S. patent application Ser. No. 07/882,231 filed May 8, 1992, abandoned, which is a continuation of U.S. patent application Ser. No. 07/295,934 filed Jan. 11, 1989 abandoned.

The present invention is related generally to the isolation and characterization of new genes and proteins. More particularly, the present invention is related to providing isolated, substantially pure, biologically active human thyrotropin (hTSH) synthesized by a cloned gene.

Thyrotropin (TSH) is a pituitary peptide hormone which regulates important body functions. However, heretofore there was no stable, reliable and economic means of synthesizing this important hormone.

SUMMARY OF THE INVENTION

It is, therefore, an object of the present invention to provide biologically active, synthetic human thyrotropin in substantially pure, isolated form.

It is another object of the present invention to provide a cloned gene which directs the expression of biologically active human thyrotropin in a suitable vector.

It is a further object of the present invention to provide an assay kit for measuring thyroid-stimulating hormone as well as other thyrotropin substances such as thyroid-stimulating immunoglobulins and the like.

It is a further object of the present invention to provide a method of diagnosing and treating human thyroid cancer.

Other objects and. advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1:
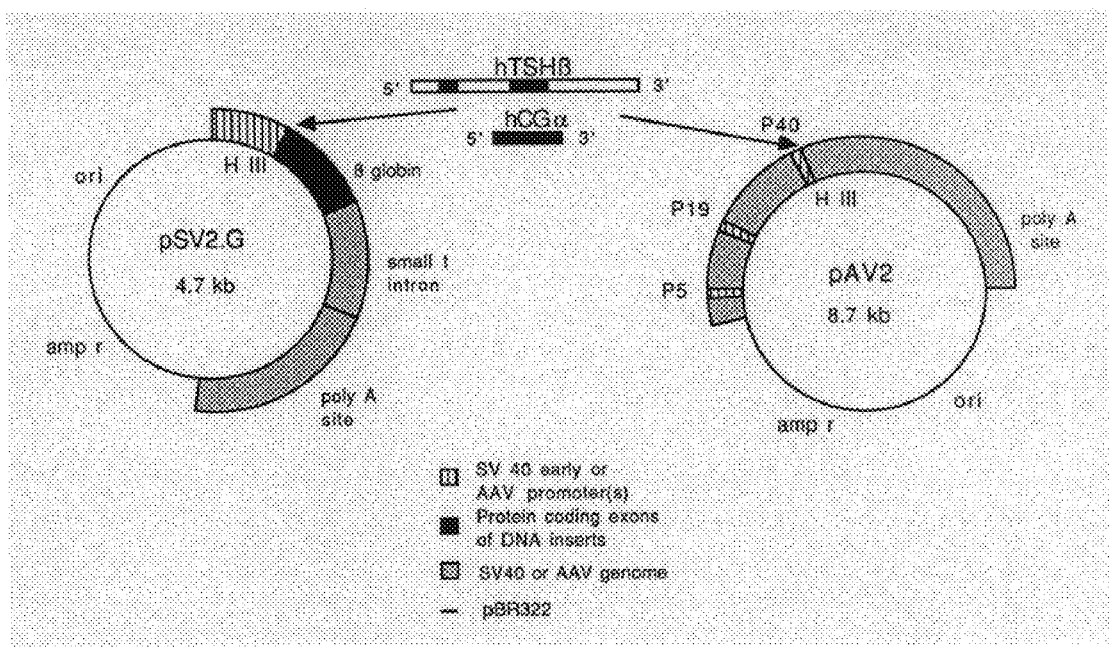
FIG. 1 shows schematic construction of the expression vectors. pSV2.G and pAV2 are pBR322 derived plasmids with the origin of replication (ori) and ampicillin resistance gene (amp r) as shown. pSV2.G contains the early promoter of SV40 upstream of the HindIII cloning site, rabbit β-globin cDNA, and poly-adenylatlon site/intron of SV40. pAV2 has the entire adenovirus-associated virus genome (4.7 kb) with its three promoters P5, P19, P40, and poly-adenylation site. The HindIII cloning site is downstream of the P40 promoter. Human TSHβ and hCGα was inserted Into the HindIII site of either plasmid, forming pAV2-hTSHβ, pAV-hCGα, pSV2.GhTSHβ, and pSV2.G-hCGα.

The above and various other objects and advantages of the present invention are achieved by the cloning of complete nucleotide sequence which directs the synthesis of biologically active human thyrotropin in a suitable expression vector and isolating substantially pure form of the synthesized hormone.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

The term "substantially pure" as used herein means as pure as can be obtained by employing standard conventional purification techniques known in the art.

The term "biologically active" as used herein means that the recombinant hormone, even though not identical in physical or chemical structure or composition as the naturally occurring hormone, yet is functionally equivalent thereto.

MATERIALS AND METHODS

Materials

Restriction and modifying enzymes were obtained from Bethesda Research Laboratories (Gaithersburg, Md.) and Pharmacia (Piscataway, N.J.). $^{52}P$ and $^{55}S$ compounds were purchased from both DuPont New England Nuclear (Boston, Mass.) and Amersham/Searle Corporation (Arlington Heights, Ill.). Gene Screen and Gene Screen Plus membranes (New England Nuclear) were used in all DNA and RNA transfer procedures. A transformation competent strain of Escherichia coli, HB101, was obtained from Bethesda Research Laboratories and used in all transformations. Oligonucleotides were purchased from the Midland Certified Reagent Company (Midland, Tex.). Cloning and propagation of DNA was done in accordance with NIH guidelines. Sephadex G-200 fine and concanavalin A-Sepharose were obtained from Pharmacia Fine Chemicals. α-Methyl glucoside and a-methyl mannoside were purchased from Sigma (St. Louis, Mo.). Human TSH, hCGα, and hTSHβ were provided by the NIDDK National Hormone and Pituitary Program (Bethesda, Md.). Protein standards were purchased from Sigma or Pierce Chemical Co. (Rockford, Ill.).

Genomic Screening

Independent recombinant phage clones ($1 \times 10^6$) of an EMBL3 human genomic leukocyte library were screened for the presence of human TSHβ using a radiolabeled mouse TSHβ cDNA obtained from W. Chin, Brigham and Women's Hospital, Harvard Medical School, Boston, MA, and two separate clones were identified. A 34 base oligonucleotide, with the same sequence as the first 34 bases of the 5'-untranslated sequence of bovine TSHβ cDNA, was 5'-end labeled with $[\tau\text{-}_{52}P]$ATP to a specific activity of $5$–$8 \times 10^6$ cpm/picomol using polynucleotide kinase; mouse TSHβ cDNA was $[\alpha\text{-}^{52}P]$ dCTP labeled with a random primer to a specific activity of $1$–$5 \times 10^9$ cpm/µg. Both were used to probe Southern blots of restriction digests of one clone.

Subcloning and Sequencing

Genomic fragments were subcloned into pUC18 and mp13 to facilitate restriction mapping and sequencing using the dideoxy chain termination method of Sanger (Sanger et al, 1977, Proc Natl Acad Sci USA 74:5463–5467).

Expression Vectors

A 621 bp hCGα cDNA (obtained from J. Fiddes, California Biotechnology Inc., Palo Alto, Calif.) was inserted downstream of the early promoter of SV40 in pSV2.G [obtained from B. Howard, NIH (Bethesda, Md.)] (Gorman et al, 1982, Mol Cell Biol 2:1044–1051) or the P40 promoter of adeno-associated virus in pAV2 (Laughlin et al, 1983, gene 23:65–73) at the HindIII site forming pSV2.G-hCGα and pAV2-hCGα (FIG. 1). HindIII linkers were ligated to a 2.0 kb PvuII fragment of the hTSHβ gene containing 277 bp of 5'-intron, both coding exons, a 450 bp intron, and approximately 800 bp of 3'-flanking DNA. It was inserted into the same HindIII sites as hCGα forming pSV2.G-hTSHβ and pAV2-hTSHβ (FIG. 1). All plasmids were subjected to multiple restriction enzyme digestions to confirm the presence of only one insert in the proper orientation.

Cell Culture

Adenovirus transformed human embryonal kidney cells (293 cells) and SV40 transformed monkey kidney cells (COS cells) were grown in a modified minimal essential (MEM) and Dulbecco's modified Eagle's medium, respectively. Both media were supplemented with 10% fetal bovine serum, 4.4 mM L-glutamine, 100 U/ml penicillin, 100 µg/ml streptomycin, and 250 ng/ml amphotericin B. Twenty-four hours before transfection, the cells were replated on 100-mm dishes at the same density ($5 \times 10^5$). On the day of transfection fresh medium was added to the cells 4 h before transfection.

Transfection

All transfections were performed using the calcium phosphate precipitation method (Graham et al, 1973, Virology 52:456–467). The precipitate was applied for 4 h, the cells were washed, and fresh medium was added. Total RNA was isolated according to the method of Cathala et al, 1983, DNA 2:329–335. The pAV2 plasmids were transfected into both 293 and COS cells in Exp 1 and into only 293 cells in Exp 2. The pSV2.G plasmids were only transfected into COS cells. When either the α- or β-subunit was transfected alone into cells, 15 µg purified plasmid were applied to each plate. When both the α- and β-subunit were cotransfected, 9 µg each purified plasmid were applied to one plate. In some cases, cells were cotransfected with pVARNA. PVARNA consists of an adenovirus type 2 DNA HindIII B fragment containing the genes for $VA_I$ and $VA_{II}$ inserted into the HindIII site of pBR322 (obtained from Ketner, Department of Biology, Johns Hopkins University, Baltimore, Md.). $VA_I$ RNA stimulates translation by inhibiting phosphorylation and inactivation of the a subunit of eucaryotic initiation factor 2 (Akusjarvi et al, 1987, Mol Cell Biol 7:549–551).

RNA Analysis, RIA, and IRMA

Northern blot analysis of total RNA from transfections was performed using standard methods (Maniatis et al, 1982, Molecular Cloning, ed 1. Cold Spring Harbor Laboratory, Cold Spring Harbor, N.Y., p 202) and manufacturer's specifications. Common human a-subunit RIA, hTSHβ-subunit RIA, and hTSH IRMA were performed in duplicate on the medium from each transfected culture (McBride et al, 1985, Clin Chem 31:1865–1867; Kourides et al, 1974, Endocrinology 94:1411–1421). The sensitivities of the assays were less than 0.03 ng/ml, less than 0.03 ng/ml, and less than 0.06 ng/ml, respectively. Cross-reactivity between the corresponding subunit and hTSH, at the measured concentration, was less than 5% in the common a and less than 2% in the hTSHβ RIA (Kourides et al, supra). In addition, at the measured free subunit concentrations, the hTSH IRMA exhibited less than 1% cross-reactivity (data not shown).

Gel and Lectin Affinity Chromatography

The apparent mol wt of hTSH synthesized in 293 cells was determined by gel chromatography on a 1.5×90-cm Sephadex G-200 fine column calibrated during each chromatography run with five protein standards (bovine thyroglobulin, BSA, ovalbumin, bovine chymotrypsinogen A, and whale myoglobin). The column was equilibrated and run at 4° C. In a buffer containing 0.12 M sodium chloride. 0.1 M borate, and 0.02% (wt/vol) sodium azide, pH 7.4. Two milliliters of fresh MEM medium containing 100 µUhTSH (WHO 80/558), 100 ng hCGα (CR-119), and 100 ng hTSHβ (AFP-3929β) were applied during chromatography of standard preparations. The column was washed and then 2 ml MEM medium from 293 cells transfected with pAV2-hCGα/pAV2-hTSHβ/pVARNA were applied. Fractions of 1.5 ml were collected at a flow rate of 6 ml/h.

The binding of hTSH synthesized in 293 cells to concanavalin A-Sepharose was also determined using methods previously described (Gesundheit et al, 1987, J Biol Chem 262:5197–5203). Samples were applied to lectin column, and 2-ml fractions were collected at a flow rate of 10 ml/h. Human TSH IRMA was common human α- and hTSHβ- subunit RIAs were performed on fractions from gel and lectin chromatography. Recovery of hTSH and its free subunits was generally greater than 90% from chromatography.

TSH Bioassay

Thyrotropic bioactivity was measured as the ability to stimulate the uptake of $^{125}$I into rat thyroid cells (FRTL5) in accordance with the procedure of Dahlberg et al, 1987, *J Clin Invest* 79:1388–1394. This assay measures human, rat, and bovine thyrotropin but not gonadotropins or free α- or TSHβ-subunits. Sample determinations were performed in duplicate and compared to two pituitary hTSH standards (World Health Organization 80/558 and National Institutes of Health I-6). Results are expressed as microunits per ml; one microunit of WHO 80/558 is equivalent to 0.09 ng of NIH I-6 purified hTSH (unpublished data).

Statistics

Significant differences in immunoassay of cell media from various control and transfected cultures were determined using Student's t test.

RESULTS

Human TSHβ Gene

A 17 kb genomic fragment was isolated by screening 1×10$^5$ recombinant phage clones. A restriction map (FIG. 1) was constructed using Southern blots of phage DNA hybridized with both a mouse TSHβ cDNA probe (lacking 5'-untranslated sequences) and a 34 bp bovine 5'-untranslated sequence probe. Two coding exons are separated by a 450 bp intron and the sequence is identical to the published partial sequence (Hayashizaki et al, 1985. *FEBS Lett* 188:394–400) (data not shown). However, the complete coding sequence was not heretofore known.

Transfection

Two experiments were performed to compare the level of mRNA and protein production between the most active adeno-associated virus promoter, P40, and the early promoter of SV40.

Table 1 shows the RIA and IRMA assay results from these two experiments. Interestingly, the 293 cells synthesized small amounts of free α-subunit (control) whose levels were increased approximately 10-fold In a transfection with the calcium phosphate precipitate but without DNA (mock) (P<0.0005). While neither transfection with pAV2-hCGα nor pVARNA increased a-production above the level of a mock transfection, the combination increased free α-levels 3- to 5-fold (P<0.0005). Thus exogenous sources of the human α-subunit were clearly important in mediating this increase. The same pattern of pVARNA increasing protein production was seen when pAV2-hTSHβ was transfected. 293 cells do not produce hTSHβ so that the medium of cells exposed to a mock or pVARNA transfection did not have measurable hTSHβ. Only the 293 cells exposed to pAV2-hTSHβ produced hTSH. When the β plasmid was transfected alone the hTSH formed was due to combination with endogenous α. Cotransfection with both α- and β-plasmids, though, increased hTSH levels 1.5- to 2-fold (P<0.05).

COS cells synthesized neither free α nor β but could synthesize hTSHβ and hTSH when transfected with the appropriate plasmids. The levels of protein production were 10- to 100-fold less than in 293 cells and were only measurable when the PVARNA plasmid was also transfected. Regardless of whether pAV2 or PSV2.G was used, protein levels were barely if at all measurable without the PVARNA plasmid.

Figure 2:
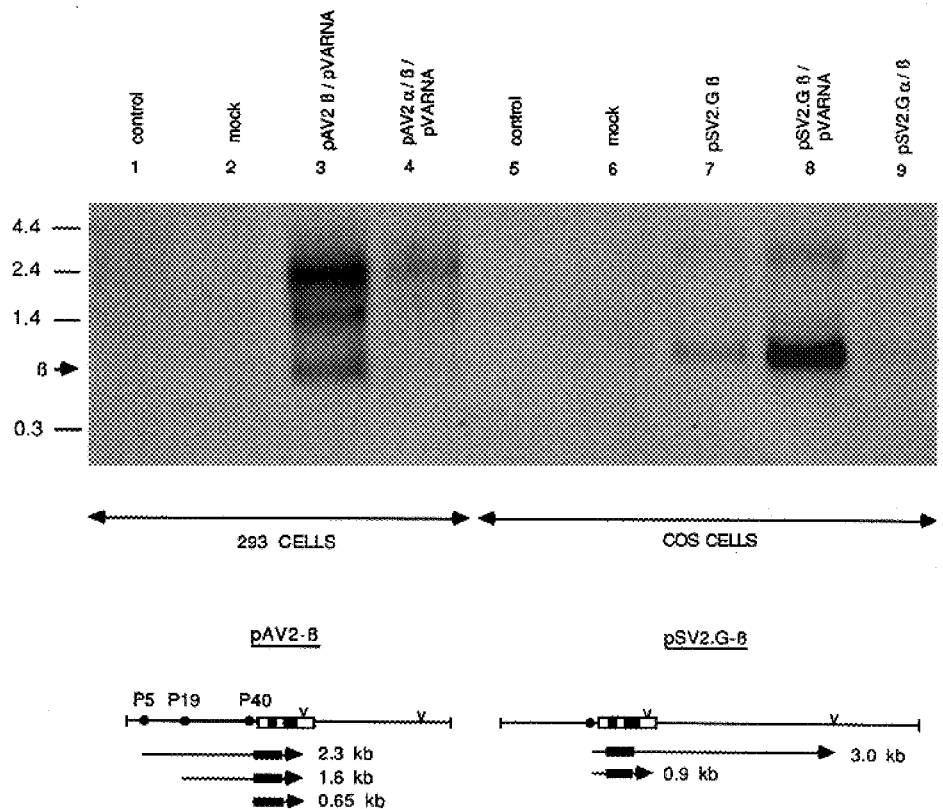
FIG. 2shows Northern blot analysis of transfected 293 and COS cells. Total cellular RNA was separated on a 1% agarose-formaldehyde gel and transferred to a nylon membrane. Forty micrograms of total RNA from a control of transfected cell culture were applied to each lane. Human CGα and hTSHβ were abbreviated α and β in construct names and in other figures. Cells that were not transfected are labeled control. Cells transfected with a calcium phosphate precipitate lacking DNA are labeled mock. Lanes 1–4 are total RNAs derived from 293 cells; lanes 5–9 are RNAs derived from COS cells. The migration position of an RNA standard in kilobases and hTSHβ mRNA from human pituitary is shown to the left of the autoradiograph. Below the autoradiograph is a simplified version of FIG. 1 showing the pAV2 and pSV2.G plasmid as a single line, the promoters as blackened circles, the 2.0 kb hTSHβ genomic fragment as a box containing two exons (blackened regions) and known polyadenylation signal-site sequences as open arrowheads. Below each construct, pAV2-β and pSV2.G-β, is the predicted RNA initiating at the specified promoter, and splicing as shown. Solid arrowheads, poly(A) tails. Predicted size in kilobases (kb) is shown to the right of each mRNA species.

FIG. 2 shows a Northern blot of total cellular RNA hybridized with the mouse TSHβ cDNA probe. In 293 cells, hTSHβ message was not detected from nontransfected (control) or from mock transfected cells. However, three RNA species of 2.3 kb, 1.6 kb, and 650 bases were noted after transfection of pAV2-hTSHβ and pVARNA (lane 3). These three bands are the same size as those predicted from pAV2-hTSHβ if transcription began at all three adeno-associated viral promoters (FIG. 2). The mRNA of 650 bases presumably represent a properly spliced hTSHβ message. Lane 4 shows the same three bands but at lesser intensity when pAV2-hCGα, pAV2-hTSHβ, and pVARNA were cotransfected. This reduction in signal intensity seen in lane 4 may have been due to the reduction in the amount of pAV2-hTSHβ transfected from 15μ to 9 μg.

Control and mock transfected COS cells also did not contain hTSHβ message. When pSV2.G-hTSHβ was transfected (lanes 7–9), a major band of 900 bases and a minor band of 3.0 kb were seen. Without being bound to any theory, it is postulated that the 900 base species could represent a mRNA with the 277 bases of 5'-intron remaining, while the 3.0 kb species could represent read through of the hTSHβ polyadenylation signal-site and use of the polyadenylation signal-site of pSV2.G (See FIG. 2).

Specific human α mRNA transcripts of appropriate size analogous to the hTSHβ mRNA above were observed in cells transfected with pAV2-hCGα (data not shown). Since the main object of this invention is protein expression, the relative contribution of human a mRNA from endogenous vs. exogenous (pAV2-hCGα) sources in 293 cells was not determined. However, the data suggest that the high level of free α-subunit observed after transfection with pAV2-hCGα/pVARNA is most likely due to mRNA from exogenous sources.

Gel and Lectin Affinity Chromatography

Figure 3:
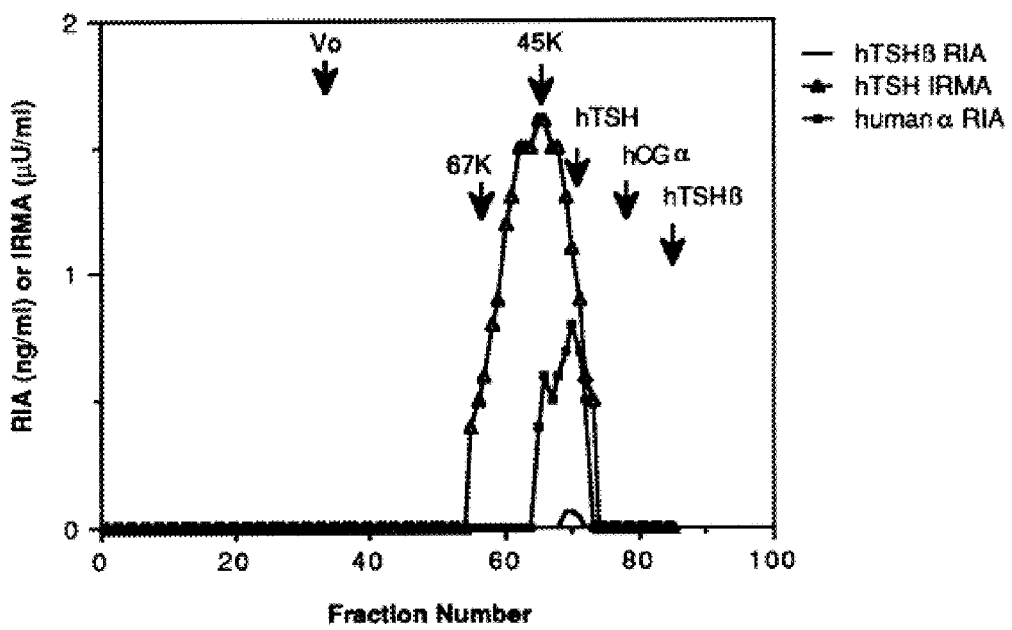
FIG. 3 shows the results of gel chromatography. Cell medium from 293 cells transfected with pAV2-hCGα/pAV2-hTSHβ/pVARNA was chromatographed on a Sephadex G-200 fine column. In addition, standard preparations of hTSH, hCGα, and hTSHβ (described in the text) were chromatographed on the same column. RIA of human α and TSHβ and IRMA for hTSH was done on each 1.5-ml fraction. Elution position of bovine thyroglobulin (void, $V_o$), BSA [67,700 (67 k)] and ovalbumin [45,000 (45 k)] is marked, as well as those of the standard preparations of hTSH, hCGα, and hTSHβ.

The apparent molecular weight of hTSH and its subunits synthesized in 293 cells after transfection with pAV2-hCGα/pAV2-hTSHβ/pVARNA was determined on a G-200 Sephadex column (FIG. 3). In addition, standard preparations of hTSH, hCGα, and hTSHβ were chromatographed on the same column. Internal protein standards had identical elution patterns between runs as determined by optical density at 280 nm. In each case, the apparent mol wt of synthetic hTSH and its subunits was larger than its corresponding standard. Specifically, synthetic hTSH displayed an apparent mol wt of 45,000 and was larger than standard pituitary hTSH. (apparent $M_r$=40,000). This clearly indicates that the recombinant TSH is not constitutively identical to the natural product. The human a and hTSHβ from transfection coeluted with the hTSH pituitary standard, and both were larger than their respective standard subunit preparation. However, in the case of free human a-subunit, the relative contribution to this chromatography pattern of endogenous a as compared to exogenous a from pAV2-hCGα cannot be determined.

The binding pattern to concanavalin A-Sepharose of synthetic hTSH from 293 cells as compared to standard human pituitary hTSH is shown in Table 2. Synthetic hTSH was glycosylated as indicated by complete binding to concanavalin A-Sepharose. The different elution pattern of standard vs. synthetic hTSH from the lectin columns is indicative of a difference at least in carbohydrate structure, again showing that the recombinant TSH (rTSH) is distinctly different from the naturally occurring TSH.

Immunoactivity and Bioactivity

Figure 4:
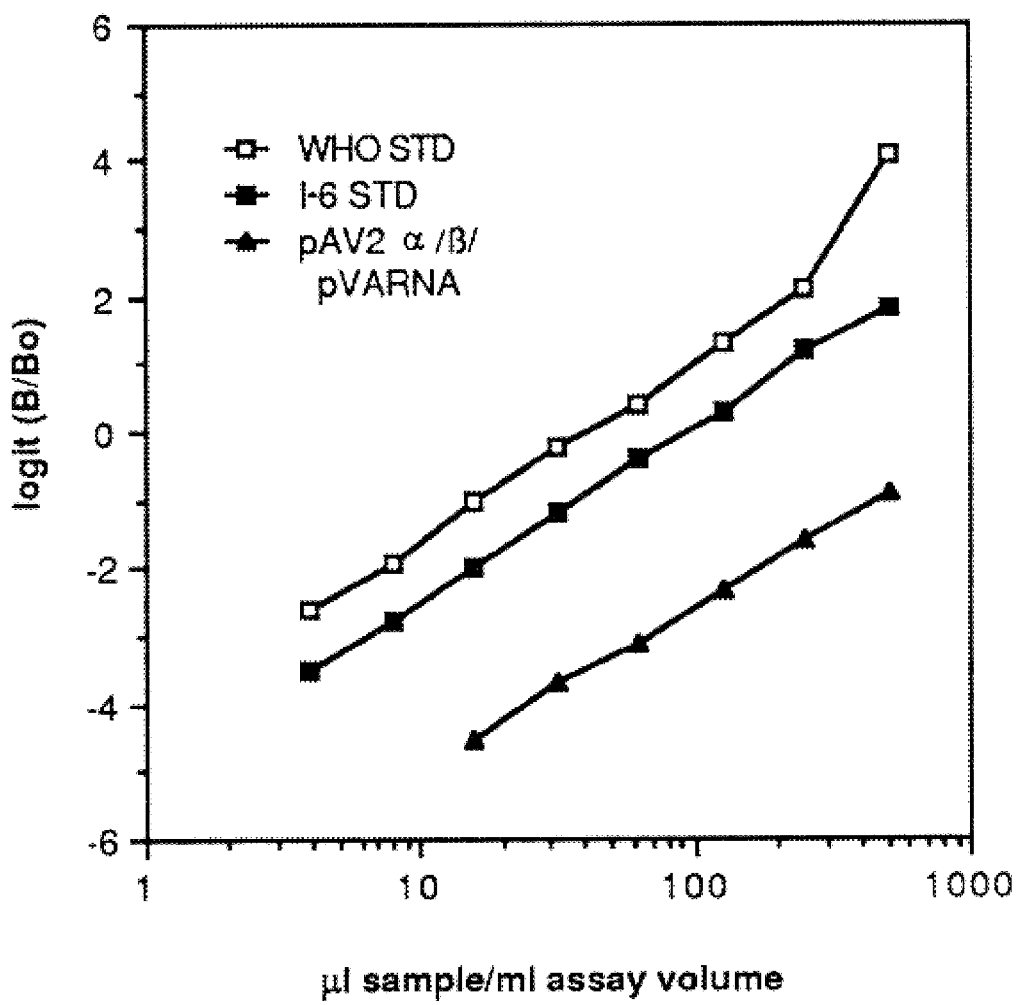
FIG. 4 shows the results of human TSH IRMA. A highly sensitive and specific hTSH IRMA was performed on two pituitary hTSH standards. World Health Organization 80/558 (WHO STD) and NIH I-6 (I-6 STD), and the medium from 293 cells after transfection with pAV2-hCGα, pAV2-hTSHβ, and PVARNA (pAV2α/β/pVARNA). A logit transformation of assay binding was plotted vs. arbitrary units of sample volume added to the assay.
Figure 5:
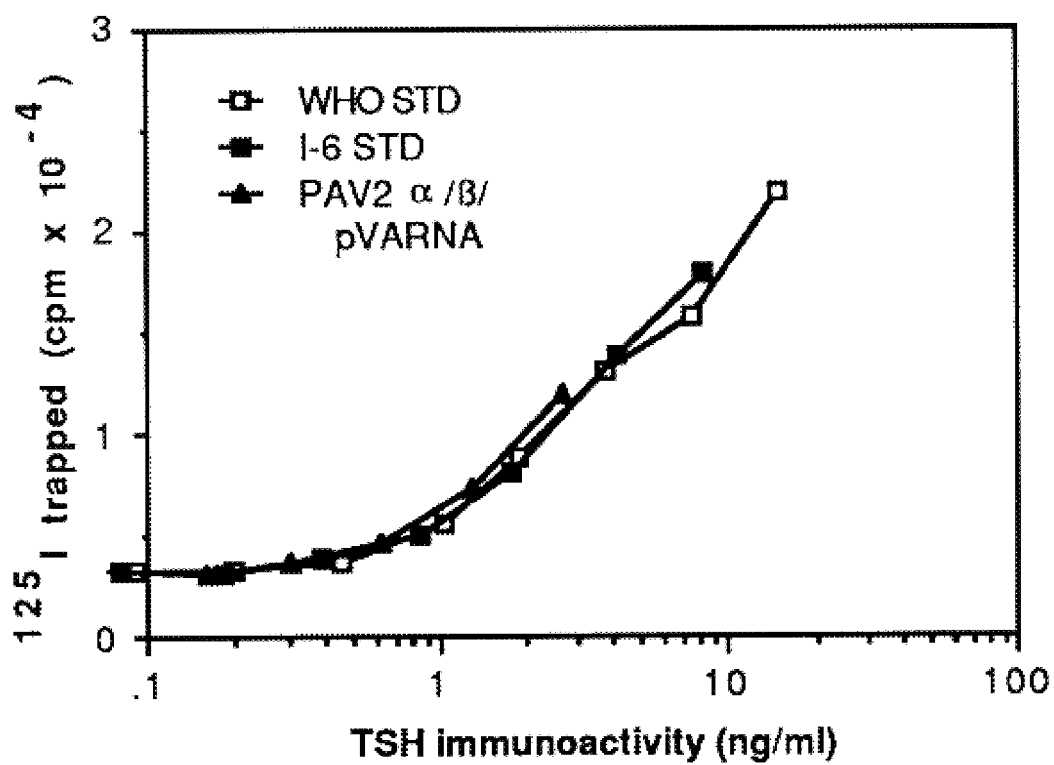
FIG. 5 shows the results of in vitro bioassay of hTSH in rat thyroid-cells. The human pituitary TSH standards and medium from transfected 293 cells used in this assay are defined in the legend to FIG. 4. This in vitro bioassay measures TSH stimulated $^{125}I$ uptake into rat thyroid cells (FRTL5). Iodide trapping by pituitary standards and medium from a transfected culture are normalized to TSH immunoactivity in an IRMA.

FIG. 4 shows that the hTSH produced in cell culture was indistinguishable from two pituitary hTSH standards in an assay involving two antibodies directed at different epitopes of the hTSH heterodimer (McBride et al, supra). The slopes were parallel over the entire range of values. FIG. 5 shows the same hTSH in a $^{125}$I trapping in vitro TSH bioassay compared to the same pituitary hTSH standards. The in vitro bioassay of standard pituitary hTSH or the cell culture product from 293 cells (pAV2-hCGα/pAV2-hTSHβ/pVARNA) was normalized to immunoreactivity In a hTSH immunoradiometric assay (IRMA) assay. The dose response and $ED_{50}$ of the standards and cell culture product were identical. In addition, the cell culture product from COS cells (pAV2-hCGα/pSV2β/pVARNA) was biologically active although the lower level of expression prevented determination of a dose response curve.

In summary, a 17 kb genomic fragment of hTSHβ has been isolated and both coding exons of this gene produced hTSHβ and hTSH in a transient expression assay. This is the first report of TSH from any species produced by gene transfection in cell culture. The expression vectors of hTSHβ included only the two coding exons, and not the 5'-untranslated exon of the gene (Wondisford et al, Mol. Endo. 2(1): 32–39, 1988).

Transient expression after gene transfection was used to test both the early promoter of SV40 or the P40 promoter of adeno-associated virus. The early promoter in COS cells produced more mRNA than the P40 promoter in 293 cells regardless of whether pVARNA was cotransfected. However, pVARNA clearly increased mRNA levels in either vector system. This suggests that in addition to increasing the rate of translation, pVARNA must either increase transcriptional rate, RNA transport, or stability.

While the pSV2.G-hTSHβ expression vector produced higher levels of hTSHβ mRNA than pAV2-hTSHβ, this mRNA was about 250 bases larger than that found in the human pituitary. The 450 bp intron was certainly spliced out since this intron In the mature message would have prevented hTSHβ protein synthesis. Also, an mRNA of appropriate size was produced by pAV2-hTSHβ indicating that the polyadenylation site in the fragment must be active. Thus, the most likely reason for a larger hTSHβ mRNA in COS cells was the lack of splicing of a 277 bp intron fragment upstream of the first coding exon. Eighteen base pairs downstream of the transcriptional start site of the P40 promoter is a consensus splice donor site which could explain why the 277 bp intron fragment would be spliced out in the adeno-associated virus vector.

The plasmid, PVARNA, increased protein production in either vector system, but the P40 promoter in 293 cells led to expression of between 10- to 100-fold more protein than the early promoter of SV40 when cotransfected with PVARNA. This is most likely due to an increased translational rate mediated by pVARNA as has been previously demonstrated for expression of other mRNAs (Akusjarvi et al, 1987, *Mol Cell Biol* 7:549–551). Of course, the possibility that the larger mRNA from pSV2.G-hTSHβ contributed to the lower protein levels from COS cells cannot be excluded.

The hTSH produced in cell culture was functionally indistinguishable from two pituitary hTSH standards in both a highly specific IRMA and in vitro bioassay. It should be noted, however, that the synthetic hTSH of the present invention was larger in size than standard pituitary hTSH on gel chromatography. Although it was glycosylated as indicated by complete binding to concanavalin A, it displayed a somewhat different pattern on lectin chromatography as compared to a standard hTSH preparation. The larger mol wt of these synthetic glycoproteins as compared to pituitary standards is most likely due to an altered glycosylation pattern such as more sialylation. In the case of hTSH, this might also reflect a β-subunit containing the 118 amino acids predicted from the nucleic acid sequence rather than the 112 found in standard hTSH purified from postmortem human pituitaries.

Transient expression is more convenient than stable integration in the analysis of a large number of expression vectors. pAV2 and pVARNA now allow transient expression of hTSH in 293 cells at levels high enough to analyze protein and glycosylation site structure-function relationships. Previously, the only information about such relationships came from studies involving chemical modifications of protein by iodination, nitration, acetylation, and carboxymethylation (Pierce et al, 1981, *Annu Rev. Biochem.*, Annual Reviews Inc., Palo Alto, Calif., pp 465–495) or inhibition of glycosylation by tunicamycin (Weintraub, et al, 1980, *J Biol Chem* 255:5715–5723). The chemical groups could themselves change protein conformation irrespective of the alteration in amino acids they produce and inhibition of glycosylation affects not only TSH but all cellular glycoproteins. Site-directed mutagenesis of the hCGα cDNA and human TSHβ-gene could directly address what regions are important for protein conformation, subunit combination, receptor binding, biological activity, and metabolic clearance without introducing chemical groups or unknown changes into the protein structure.

The availability of substantially pure rTSH now makes the diagnosis and treatment of human thyroid cancer and the determination of the level of TSH a reality.

Currently, the only available method to diagnose and treat human thyroid cancer involves making patients hypothyroid and allowing their own endogenous human TSH to rise after several weeks to stimulate the uptake of $^{151}$I into the cancer. Such stimulation is used as a diagnostic test to localize the tumor by scanning and is subsequently used to treat the cancer by giving large doses of $^{151}$I. All of the diagnostic tests and therapies depend on high levels of human TSH. However, the technique of producing endogenous hypothyroidism has disabling side effects including lethargy, weakness, cardiac failure, and may also lead to a rapid growth of the tumor over the several week period of treatment. In contrast, if a desirable form of synthetic human TSH were available, patients could be treated while they were euthyroid by giving exogenous injection of the TSH. However, presently it is not feasible to give exogenous TSH because there is not enough natural product from available human pituitaries collected at autopsies. Furthermore, even if available, the human pituitaries have been found to be contaminated with viruses and the National Pituitary Agency has forbidden the use of the natural product for any human diagnostic or therapeutic studies. This is true for all human pituitary hormones including human growth hormone which is now exclusively marketed as a synthetic product. However, the technology that was applicable for human growth hormone (a non-glycoprotein) is not at all applicable for human TSH (a glycoprotein hormone of two glycosylated subunits). As has been described herein supra, only the methodology described herein relating to transfection and proper glycosylation of each subunit in mammalian cells produces a desirable biologically active rTSH material. Moreover, it has been found that the altered glycosylation pattern that can be achieved with the cells, as described in the methodology of the present invention, produces a longer acting human thyrotropin which is particularly suited for the diagnosis and treatment of thyroid cancer.

The diagnosis and treatment of thyroid cancer involves first purifying the synthetic TSH from large volumes of tissue culture media harvested from approximately ten billion cells over two to four weeks. Using a chemically defined medium to reduce protein contaminants as is well known in the art, synthetic human TSH, which represents about five. to ten percent of all the protein secreted into the medium, can be obtained. The human TSH thus obtained is then purified by a combination of standard techniques including immunoaffinity chromatography, HPLC exclusion chromatography (repeated two to three times) followed by dialysis and concentration by ultrafiltration, lyophilization and the like. The purified human TSH is then tested in animals to assure its efficacy as well as freedom from any unexpected toxicity. The synthetic TSH is then tested in patients in clinical trials using different doses to determine the optimal doses to achieve maximal uptake into the tumor for both diagnosis and treatment with $^{151}$I. During initial try-outs for diagnosis, one to two administrations of about 100 μg, while during therapy three to six doses of about 100 to 200 μg may be administered, but the optimal dose schedule is determined by the results of the clinical trials. It is noted that all of these procedures are accomplished while the patient is still euthyroid without producing any of the disabling side effects of hypothyroidism which are otherwise encountered in the methods heretofore available.

When the optimal uptake of $^{151}$I has been established, patients may be treated with doses of about 50 to 400 mCi of $^{151}$I and the effect of therapy assessed by subsequent $^{151}$I diagnostic tests as well as conventional x-rays, CAT scans, measurement of serum thyroglobulin and the like. Of course, $^{151}$I-labeled rTSH, which is produced by standard methodology well known in the art, can be appropriately utilized in the procedures mentioned above.

It is estimated that there will occur about ten thousand new cases of thyroid cancer in the United States each year and a very large prevalence of older cases of this cancer require repeated diagnostic and therapeutic intervention which are currently unsatisfactory. Availability of synthetic human TSH as taught herein, even at a cost of $50.00 to $100.00 per injection, will still be a relatively inexpensive part of the complete evaluation and therapy for this difficult, but curable cancer.

Another advantage of the product of the present invention is to provide assay components for human thyrotropin using the technique of radioimmunoassay. Certain immunoassay kits are presently available, but the reagents therein are again derived from a very short supply of natural product. Moreover, the natural product varies greatly depending on the source of the human pituitaries as well as the degree of degradation that occurs during autopsy. This has led to considerable variation among commercially available kits with disagreements in results of the TSH testing among various kits. In contrast, the present invention, for the first time, provides a virtually unlimited supply of a stable preparation of synthetic TSH allowing kit manufacturers to have a universal standard preparation and a virtually identical and inexhaustible supply of the reagents. This would allow world wide consistency of dosage and lead to much needed standardization in the measurement of human TSH which is vital in the assessment of thyroid function in humans. This is accomplished by labeling the rTSH with radioactive iodine ($I^{131}$, $I^{125}$)or another suitable labeling material such as chemoluminiscent or fluorescent labels and by producing antibodies to the pure product by either polyclonal or monoclonal techniques which are well known in the art and providing inexhaustible supplies of immunoglobulins without significant interfering cross-reactivity with other hormones. The antibodies are then formulated in classic radioimmunoassay kits which are supplied to the manufacturers to be used in a variety of standard assay methodologies (RIA, IRMA, Sandwich Assays and the like).

There are various other advantages of rTSH. Tests have demonstrated that it is possible to modify the TSH by expressing the hormone in various cell lines leading to altered glycosylation patterns. Moreover, using the technique of site-directed mutagenesis whereby individual bases in the DNA are changed, products are obtained with altered biologic function such as prolonged or decreased half life, as well as competitive antagonists that bind to the TSH receptor and actually block TSH function. Such competitive antagonists are useful in a novel way to treat diseases such as TSH-induced byperthyroidism as well as Graves' disease which is caused by auto-antibodies to the TSH receptor. The function of these abnormal stimulators would be blocked by the competitive antagonist that we have already shown to be active at the cellular level. Moreover, using various long-acting and short-acting preparations, superagonists can be prepared which would be particularly stimulating to thyroid function, and superantagonists can be prepared which would be particularly inhibitory of thyroid function. In this manner, thyroid function can be controlled in many different types of disease of thyroid overactivity or underactivity. It should be noted that these completely novel approaches are feasible only because of the availability of the synthetic TSH by the methodology of the present invention because, for the reasons mentioned above, the natural product is prohibited from such in vivo use.

It has also been discovered that modifications of the transfection process greatly enhances the amount of TSH production by mammalian cells. For example, instead of using TSH-β gene constructs containing only the 2nd and 3rd exons (the 2 coding exons), a new construct is made by adding the first untranslated exon of TSH-β. The inclusion of this untranslated TSH-β exon greatly increases TSH production. Without being bound to any specific theory, it is postulated that the enhanced TSH production occurs by increased transcription rate and/or mRNA stability. Moreover, it has been discovered that an excess of the c gene in a ratio of about 3 to 5 times greater than the β gene, yields high rate of TSH production (10–50 mg/month), close to commercial scale production.

A standard concentration curve utilizing anti-rTSH antibodies is established to determine the amount of TSH in a sample by conventional immunological assays.

In summary, a recombinantly made synthetic TSH has been made which, even though constitutively distinct from the natural product, possesses functional properties similar to the natural product and is useful for diagnostic as well as therapeutic purposes.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for producing recombinant human TSH comprising the steps of:
   a) transfecting a eukaryotic cell with an expression vector, wherein said expression vector comprises a contiguous genomic fragment of the human thyrotropin (TSH) β-subunit gene wherein the fragment comprises both coding exons of the TSH β-subunit gene separated by the intron;
   b) culturing said transfected cell under conditions that allow said vector to direct the machinery endogenous in said eukaryotic cell to perform the splicing necessary for expression of mRNA to bring about the production of TSH β-subunit and that allow for the production of TSH α subunit for combination therewith; and c) recovering substantially pure recombinant human TSH.

2. A method for producing recombinant human TSH comprising the steps of:

a) transfecting a eukaryotic cell with an expression vector, wherein said expression vector comprises a contiguous genomic fragment of the human thyrotropin (TSH) β-subunit gene wherein the fragment comprises both coding exons of the TSH β-subunit gene separated by the intron and further comprises the 5' untranslated exon;

b) culturing said transfected cell under conditions that allow said vector to direct the machinery endogenous in said eukaryotic cell to perform the splicing necessary for expression of mRNA to bring about the production of TSH β-subunit and that allow for the production of TSH α subunit for combination therewith, and c) recovering substantially pure recombinant human TSH.

3. The method of claim 1 wherein said TSH α-subunit is about 3 to 5 times in excess of said TSH β-subunit.

4. The method of claim 2 wherein said TSH α-subunit is about 3 to 5 times in excess of said TSH β-subunit.

* * * * *